United States Patent [19]

Matsuo et al.

[11] Patent Number: 5,338,830
[45] Date of Patent: Aug. 16, 1994

[54] BIOLOGICALLY ACTIVE PEPTIDE DERIVED FROM CHICKEN (CHICKEN CNP)

[75] Inventors: Hisayuki Matsuo, 5-15-141, 5-chome, Onoharahigashi, Minoo-shi, Osaka; Kenji Kangawa, Miyazaki; Naoto Minamino, Osaka, all of Japan

[73] Assignees: Suntory Limited; Hisayuki Matsuo, Osaka

[21] Appl. No.: 754,947

[22] Filed: Sep. 4, 1991

[30] Foreign Application Priority Data

Sep. 7, 1990 [JP] Japan .................. 2-238293

[51] Int. Cl.$^5$ .................. C07K 7/00; A61K 37/02
[52] U.S. Cl. .................................................. 530/326
[58] Field of Search ........................ 530/326; 514/13

[56] References Cited

U.S. PATENT DOCUMENTS

| | | | |
|---|---|---|---|
| 4,904,763 | 2/1990 | Matsuo et al. | 530/324 |
| 5,114,923 | 5/1992 | Seilhamer et al. | 514/12 |

OTHER PUBLICATIONS

Arimura et al. Biochem. Biophys. Res. Commun. (1991) 174(1) 142–8.
Minamino et al. Pept. Chem. (1991) 28 367–72.
Nakao et al, Chemical Abstracts, Columbus, vol. 113, No. 21, Nov. 19, 1990.
Arimura et al., Chemical Abstracts, Columbus, vol. 114, No. 13, Apr. 1, 1991.
Minamino et al, Chemical Abstracts, Columbus, vol. 115, No. 7, Aug. 19, 1991.
Minamino et al; C–Type Natriuretic Peptide (CNP); Biochemical and Biophysical Research Communications; vol. 168, No. 2, 1990.
Minamino et al.; N–Terminally Extended Form of C–Type Natriuretic Peptide (DNP–53) Identified in Porcine Brain; vol. 170, No. 2, 1990.

*Primary Examiner*—Merrell C. Cashion, Jr.
*Assistant Examiner*—Carol A. Salata
*Attorney, Agent, or Firm*—Cushman Darby & Cushman

[57] ABSTRACT

A novel peptide that exhibits a natriuretic action and a vasodepressor activity, and hence, that is applicable as a diagnostic reagent. The novel peptide is manufactured by the procedure of genetic engineering as well as by the methods of purification from chicken brains or by chemical synthesis.

1 Claim, 5 Drawing Sheets

Fig. 5

```
         1                            10                        20
A-type
  S-L-R-R-S-S-           -C-F-G-G-R-M-D-R-I-G-A-Q-S-G-L-G-C-N-S-F-R-  Y- :  porcine α-ANP
  S-L-R-R-S-S-           -C-F-G-G-R-I-D-R-I-G-A-Q-S-G-L-G-C-N-S-F-R- -Y :  rat α-ANP
  S-S-D-C-F-G-            -S-R-I-D-R-I-G-A-Q-S-G-M-G-C- -G-  -R-R-F:  frog ANP-24

B-type
  S-P-K-T-M-R-D-S-G-     -C-F-G-R-R-L-D-R-I-G-S-L-S-G-L-G-C-N-V-L-R-R-Y:  porcine BNP-32
  M-M-R-D-S-G-           -C-F-G-R-R-I-D-R-I-G-S-L-S-G-M-G-C-N-G-S-R-K-N:  chicken α-NP C-type
  G-L-S-K-G-             -C-F-G-L-K-L-D-R-I-G-S-M-S-G-L-G-C        :  porcine CNP
  G-L-S-R-S-             -C-F-G-V-K-L-D-R-I-G-S-M-S-G-L-G-C        :  chicken CNP
                                                              20
```

5,338,830

BIOLOGICALLY ACTIVE PEPTIDE DERIVED FROM CHICKEN (CHICKEN CNP)

BACKGROUND OF THE INVENTION

1. Field of the Invention:

The present invention relates to a novel biologically active peptide of chicken which has a natriuretic action and a vasodepressor activity. More particularly, the invention relates to a process for isolating, identifying and utilizing a novel biologically active peptide which belongs to C-type natriuretic peptide.

2. Prior Art:

Recently, various peptides, which are known as natriuretic peptides (NP), have been identified and isolated from the atrium and brain of mammals. At present, these NPs can be classified into one of three types, A-type natriuretic peptide (ANP), B-type natriuretic peptide (BNP) and C-type natriuretic peptide (CNP), on the basis of the homology of the primary amino acid sequences and the structures of precursors thereof.

Among them, ANP and BNP are also referred to as an atrial natriuretic peptide and a brain natriuretic peptide, respectively, since ANP and BNP were first isolated and identified from the atrium and brain, respectively (Matsuo, H. and Nakazato, H., *Endocrinol. Metab. Clin. North Am.*, 16, 43, 1987; Sudoh, T. et al., *Nature*, 332, 78, 1988). However, it has turned out that ANP exists not only in the atrium but also in the brain, and BNP likewise exists not only in the brain but also in the atrium. Moreover, both ANP and BNP exhibit a natriuretic action and a vasodepressor activity. Therefore, it has been clarified that ANP and BNP respectively act as a hormone which regulates the homeostatic balance of body fluid volume and blood pressure of mammals, and at a neuro transmitter in the brain.

Whereas, CNP was isolated very recently from a porcine brain and characterized as a new type of NP which does not belong to any of ANP and BNP (Sudoh, et al., *Biochem. Biophys. Res. Commun.*, 168, 863, 1990). CNP consists of 22 amino acid residues, and contains 2 cystein residues like ANP and BNP. Thus, the two cystein residues form an intramolecular disulfide bond, and the molecule has a cyclic structure consisted of 17 amino acid residues. Furthermore, the primary amino acid sequence constructing the cyclic structure of CNP was found to be highly homologous to those of ANP and BNP. The structure of CNP is characteristic in that it has no tail, while both ANP and BNP have a tail which consists of several amino acid residues added to the C-terminal of said cyclic structure. In other words, the C-terminal of CNP ends with a cystein residue. Thus, it has turned out that the structure of CNP differs from that of ANP or BNP in spite of the homology in other respects, and that CNP is a new type of NP since CNP exhibits a natriuretic action and a vasodepressor activity, and further shows a specific activity higher than ANP or BNP in relaxation of intestinum rectum specimens of chickens.

Therefore, it has been understood that various NP peptides, which can be classified into at least three different types, exist in mammals at present, and that these peptides participate in regulating the homeostatic balance of body fluid volume and blood pressure. Until now, details of CNP in terms of the distribution in the body and the physiological function were not as clear as in ANP and BNP.

On the other hand, the existence of NP peptides in non-mammal vertebrates has already been confirmed. Until now, however, only frog ANP, chicken NP and eel ANP have been isolated and characterized. The information about NP in non-mammals is less comprehensive than that for mammals (Sakata, J., Kangawa, K. and Matsuo H. *Biochem. Biophys. Res. Commun.*, 155, 1338–1345, 1988; Miyata, A., Minamino, N., Kangawa, K. and Matsuo, H. *Biochem. Biophys. Res. Commun.*, 155, 1330–1337, 1988; Takei, Y., Takahashi, A., Watanabe, T. X., Nakajima, K. and Sakakibara, S. *Biochem. Biophys. Res. Commun.*, 164, 537–543, 1989).

The present inventors have already established a highly sensitive assay system of CNP by preparing a specific antibody toward CNP and developing a radioimmunoassay (RIA) system using the antibody (Japanese Patent Application No. 186583/90). Moreover, they found that a peptide (hereunder ir-CNP), exhibiting an immunological activity toward the anti-CNP antiserum, existed in chicken brains by searching for tissues of vertebrates other than mammal with the RIA system. Until now, however, isolation and characterization of a peptide belonging to CNP from aves have not been reported.

SUMMARY OF THE INVENTION

An object of the present invention is to isolate and characterize a novel NP from chickens, particularly the one which belongs to CNP differing from the known chicken NP, and to establish a method of providing the novel NP.

Another object of the invention is to clarify the physiological function of CNPs by finding and studying a novel peptide which belongs to CNP.

BRIEF DESCRIPTION OF THE DRAWINGS

FIG. 3b is a graph showing the agreement of elution times between chemically synthesized cCNP and native cCNP, obtained in Example 1, in a HPLC performed under the similar conditions as in FIG. 3a.

FIG. 5 is an illustration of the amino acid sequences of the different types of ANP, BNP and CNP, showing the homology of the primary amino acid sequences of these peptides (see SEQ ID NOS: 1, 2, 3, 4, 5, 6, and 7).

DETAILED DESCRIPTION OF THE INVENTION

The present inventors searched for a novel NP from chickens using the RIA system, which was developed by the inventors as mentioned above, and is capable of detecting CNP at a high sensitivity.

Figure 3A:
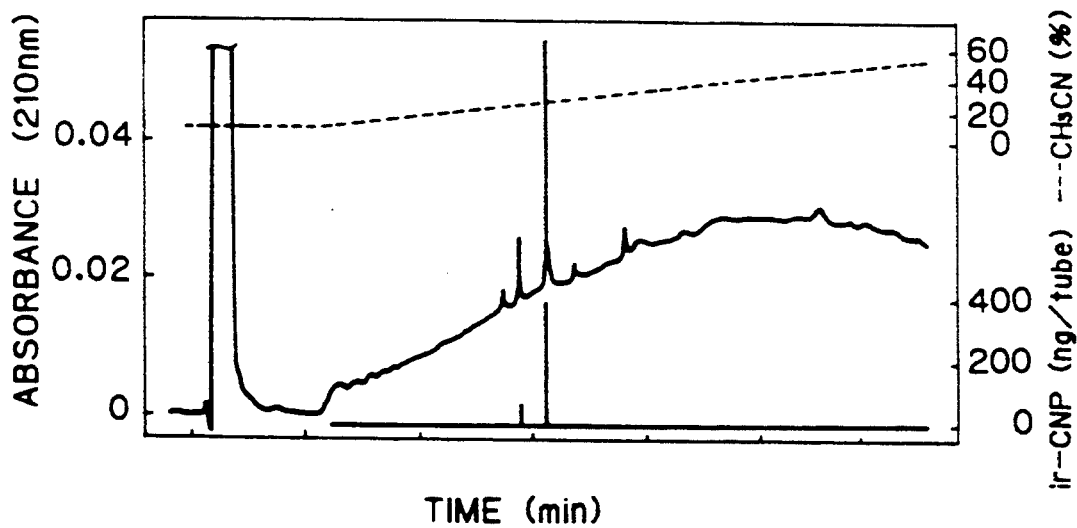
FIG. 3a is a graph showing the elution pattern when the ir-fraction, eluted from 42 to 44 minutes in the CM cation exchange HPLC in FIG. 2, was further purified by a reverse phase HPLC with μ-bondasphere C-18.

A peptide capable of reacting toward an anti-CNP antibody was successfully purified as a single, pure substance as shown in FIG. 3a by homogenizing chicken brain in a suitable acidic solution such as glacial acetic acid, followed by a combination of different methods which are commonly used in the purification of peptides in order to purify peptide fractions having molecular weight of about 3,000, using positive reaction in said RIA system as the measure of the desired peptide.

A sample of the purified peptide was then reduced, the cystein residue were carboxymethylated and the amino acid sequence of this peptide was determined. As a result, it was found to be a novel peptide having the following structure:

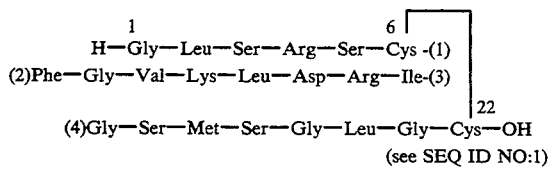

(see SEQ ID NO:1)

wherein (1) and (2), (3) and (4) directly bind, and the cystein residues (Cys) at positions 6 and 22 form an intramolecular disulfide bond.

The novel peptide will be hereinafter referred to as chicken C-type natriuretic peptide or cCNP.

The cCNP has been found to be a novel peptide which belongs to CNP by comparing both the amino acid sequence and the structure with those of the known NPs which are classified into one of three types (see FIG. 5). Namely, cCNP consists of 22 amino acid residues like known CNPs (e.g. porcine CNP in FIG. 5), and further does not have a C-terminal tail structure in keeping with the structural characteristic of CNP. Moreover, cCNP was found to be the most homologous to CNP when the amino acid sequence of cCNP was compared with ANP, BNP and CNP. Actually, 19 out of 22 amino acid residues in the primary amino acid sequence of cCNP were identical to CNP. Furthermore, the nature (such as the basicity and the hydrophobicity of amino acids) of the remaining three amino acid residues was found to be substantially identical between cCNP and CNP. In addition, cCNP was found to exhibit a natriuretic action and a vasodepressor activity in rats.

From this evidence, cCNP has turned out to be a novel peptide which belongs to CNP, resulting in the completion of the present invention.

Now that the structure of cCNP has been disclosed herein, cCNP may be manufactured by a genetic engineering method as well as the method shown in the present specification wherein cCNP is purified from chicken brains, and further by use of a chemical synthesis. In addition, since cCNP exhibits a significant natriuretic action and a vasodepressor activity, cCNP is expected to be applicable for drugs.

The following Examples are provided to further illustrate the present invention.

EXAMPLE 1

Isolation and purification of cCNP from chicken brain

In the present specification, each purification step was monitored by the RIA hereinbefore described.

Figure 1:
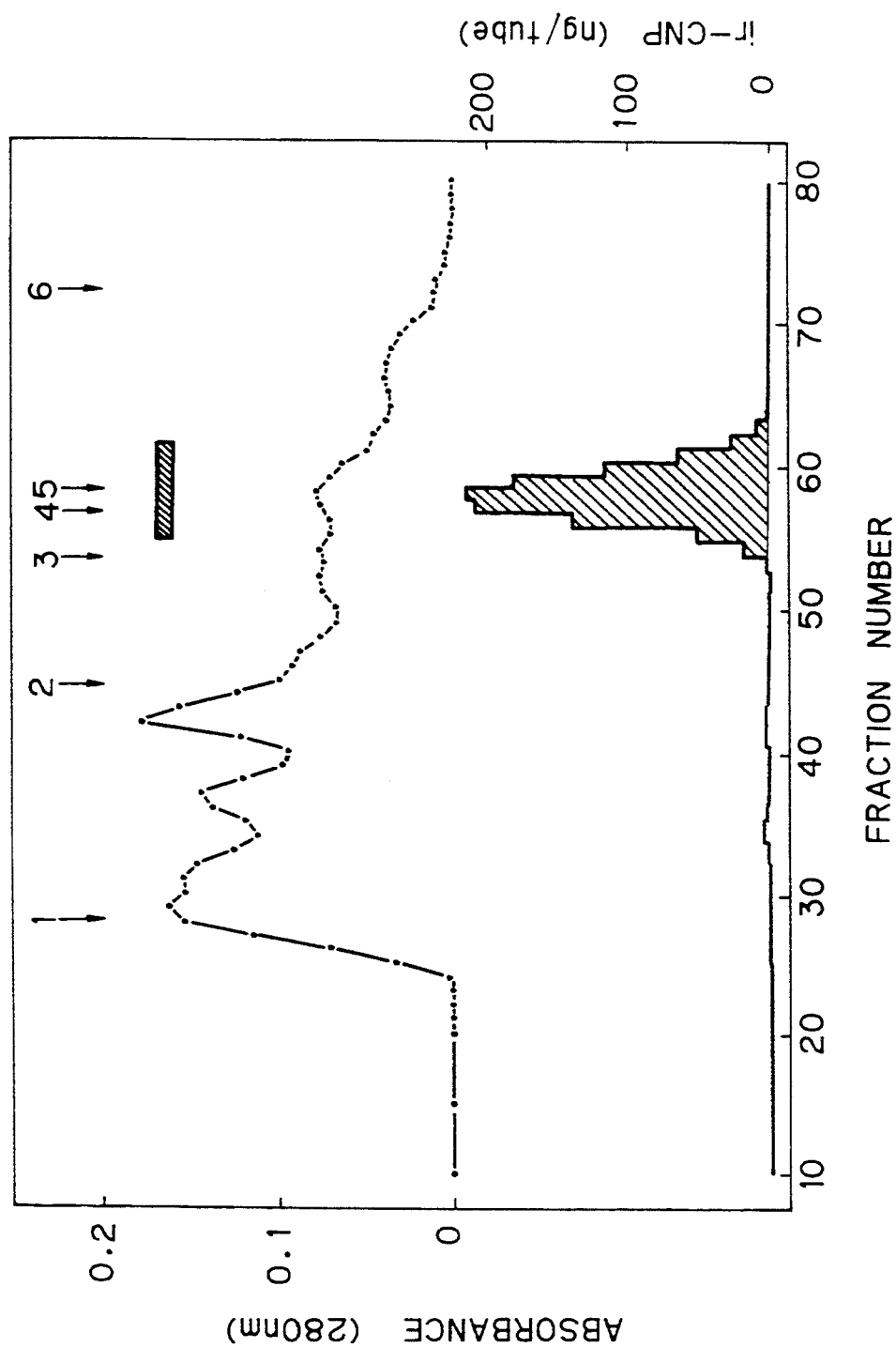
FIG. 1 is a graph showing the elution pattern and the immunological reactivity of each fraction toward an anti-CNP antiserum when the fraction (SP-III) from chicken brain extract was further fractionated with Sephadex G-50.

Brain sections weighing 417 grams were removed from 150 chickens, and, after cutting into pieces, were treated with three times the volume (V/W) of boiled water for 10 min to inactivate proteases. After cooling, glacial acetic acid was added up to a final concentration of 1M, and the tissue was homogenized for 5 min. with a Polytron mixer. Subsequently, the homogenate was divided into a residual fraction and a supernatant fraction by centrifugation (20,000×g, 30 min). Aceton was added to the supernatant fraction to make final concentration of 66%, whereby precipitation occurred. The supernatant was centrifuged, dried in vacuum, diluted with twice volume of water, and applied to HPLC C-18 column (90 ml Chemco LC-SORB SPW-C-ODS). After washing the column with 0.1% trifluoroacetic acid (TFA), peptides which adsorbed on the column were eluted with 60% acetonitrile ($CH_3CN$) containing 0.1% trifluoroacetic acid (TFA). The eluate was concentrated under reduced pressure, dissolved in 1M acetic acid, and applied to an ion exchange chromatography using a SP-Sephadex C-25 column ($H^+$-form, 1.4×15 cm; Pharmacia) equilibrated with 1M acetic acid. Peptides which adsorbed on the column were eluted with 1M acetic acid, 2M pyridine and then 2M pyridine-acetic acid (pH 5.0). The eluted fractions, which will hereafter be referred to as SP-I, SP-II and SP-III, were freeze-dried, separately. Eighty percent of the peptide components, which exhibited an immunological reactivity to the anti-CNP antiserum in said RIA system, was found to be recovered in the fraction SP-III. A 140 mg portion (dry weight) of the obtained SP-III fraction was subjected to gel filtration using a Sephadex G-50 column (fine, 3.0×152 cm; Pharmacia). The gel filtration pattern is shown in FIG. 1. The solvent was 1M acetic acid, the fraction size was 15 ml/tube, and the flow rate was 20 ml/h. In FIG. 1, each arrow indicates the eluted positions of 1) bovine serum albumin, 2) pBNP-32, 3) pBNP-26, 4) α-pANP [4–28], 5) pCNP, and 6) and NaCl, and the boxes with slant lines indicate fractions which exhibited immunological reactivity to the anti-CNP antiserum in said RIA system (ir-CNP).

The immunologically reactive fractions (fraction numbers 55–61) were pooled and freeze-dried (dry weight 19 mg), and further purified by HPLC using a CM cation exchanger (TSK gel CM-2SW: 7.6×300 mm, Tosoh). Using the following solvents (A) and (B), the elution was performed with linear density gradients in which the ratio of (A):(B) changed 100:0 to 50:50 for the first 80 min and 50:50 to 0:100 for the last 20 min at a flow rate of 2.0 ml/h.

(A) 10 mM $HCOONH_4$ (pH 6.6):$CH_3CN$=90:10 (V/V)

(B) 1.0 mM $HCOONH_4$ (pH 6.6):$CH_3CN$=90:10 (V/V)

Figure 2:
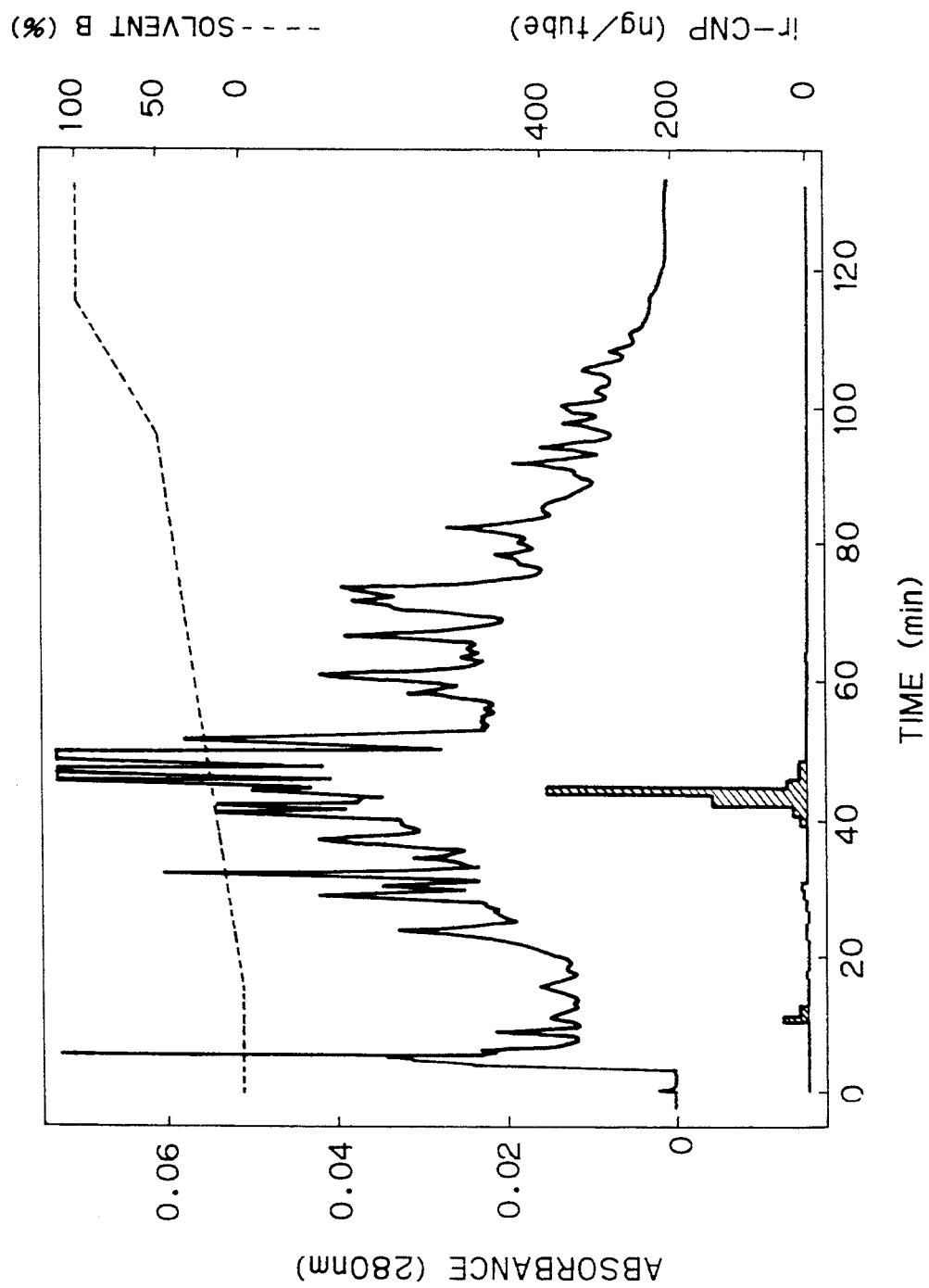
FIG. 2 is a graph showing the elution pattern and the immunological reactivity of each fraction toward an anti-CNP antiserum when the active fraction, eluted from the Sephadex G-50 column in FIG. 1, was further purified by a CM cation exchange HPLC.

The elution pattern is shown in FIG. 2. In this chromatography, although ir-CNP was eluted in a single peak in elution time 42–44 min, it was not single as a peptide. Therefore, ir-fractions were together freeze-dried, dissolved in a 0.1M sodium phosphate buffer, pH 7.4 containing 0.002% Triton X-100, and further purified using an immunoaffinity column (500 μl) of anti-α-

ANP immunoglobulin G (IgG). The immunoaffinity chromatography was already reported by the present inventors for α-ANP [4–28] and α-ANP [5–28] (Ueda, S., Sudoh, T., Fukuda, K., Kangawa, K., Minamino, N. and Matsuo, H. *Biochem. Biophys. Res. Commun.*, 149, 1055–1062, 1987). The peptides which were adsorbed on the column were eluted with a 1M CH₃COOH solution containing 10% CH₃CN, subjected to a reverse phase HPLC using μ-Bondasphere C-18 (3.9×150 mm, 300 A, Waters), and eluted with 10–60% CH₃CN in 0.1% TFA, over 60 min at a flow rate of 1.0 ml/min. As shown in FIG. 3a, most of the ir-CNP activity existed in the fraction eluted about 31 min, and the activity peak corresponded to the main peak of the peptide in the chromatography. Thus, the substantially pure peptide (CNP) could be obtained.

The yield of the purified cCNP, as estimated on the basis of the height of the peak and the immunological reactivity in the reverse phase HPLC in FIG. 3a, was about 180 pmol (400 ng) starting from 417 g of chicken brain.

EXAMPLE 2

Determination of the structure of CNP

A. S-carboxymethylation of cCNP and determination of the primary sequence

About 135 pmol of cCNP, which was obtained in Example 1, was incubated with 20 mM DTT in a 0.5M Tris-HCl buffer, pH 8.5 at 37° C. for 4 hours, and then S-carboxymethylated cCNP, i.e., (RCM) cCNP was obtained following the treatment with sodium monoiodoacetic acid, added at 60 mM, for 20 min.

The (RCM) cCNP was subjected to a reverse phase HPLC using μ-Bondasphere C-18 (3.9×150 mm, 300 A, Waters) as used in the final step of Example 1, and purified by elution over 60 min at a flow rate of 1.0 ml/min with a linear density gradient of 10–60% acetonitrile.

Figure 4:
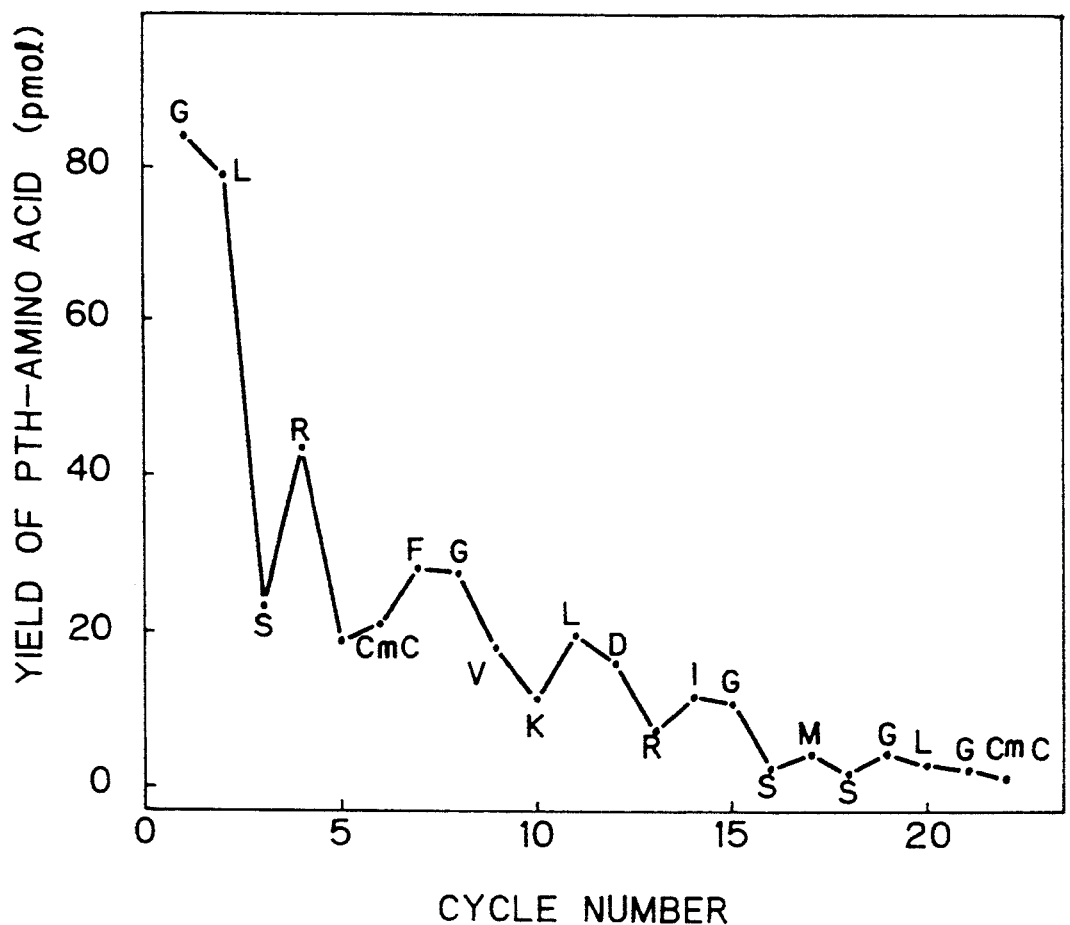
FIG. 4 is a graph showing the amino acid sequence and the yield of PTH-amino acid in each cycle in the sequence analysis of (RCM) cCNP by Edman degradation.

Subsequently, the obtained (RCM) cCNP was applied to an auto amino acid sequencer (Applied Biosystems 470A/120A), and the primary amino acid sequence was analyzed by Edman degradation. The results are shown in FIG. 4. In FIG. 4, each amino acid residue is expressed by a capital one letter code, and Cm indicates a S-carboxymethyl cystein residue. Based on these results, the primary amino acid sequence of (RCM) cCNP was determined (See FIG. 5).

B. Chemical synthesis of cCNP and determination of the manner of the S—S bond

Figure 3B:
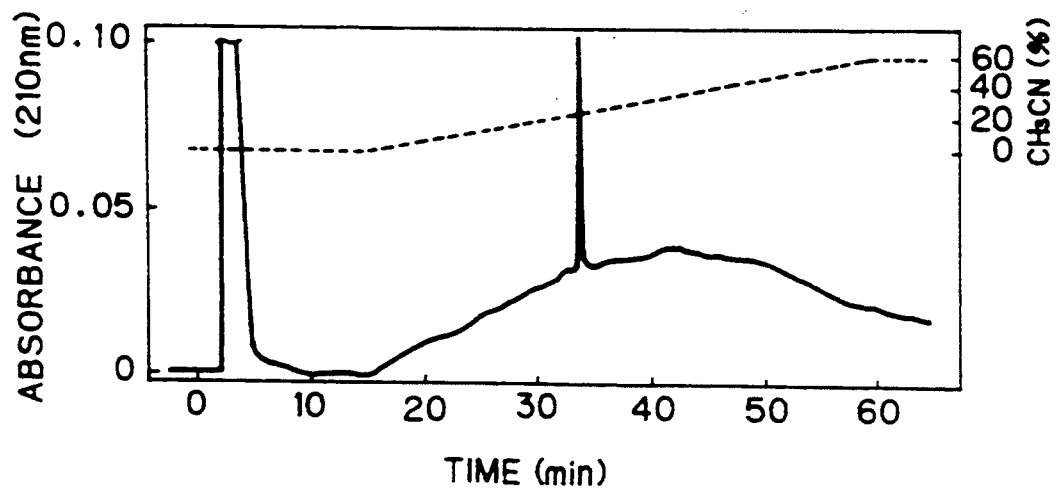

In accordance with the primary amino acid sequence determined in Example 2.A, a peptide having the primary amino acid sequence of cCNP was synthesized by the solid phase method using a peptide synthesizer (Applied Biosystems 430A). In the synthesis, 4-methylbenzyl group was used as a protective group for cystein residues. After complete deprotection with HF, an intramolecular S—S bond was formed by treating the SH groups in the cystein residues at positions 6 and 22 with K₃Fe(CN)₆. The structure of the resulted cCNP was confirmed by amino acid analysis and amino acid sequence analysis. Since the synthetic cCNP showed the same elution time as the natural cCNP obtained in Example 1 as shown in FIG. 3b, and also exhibited a positive relaxant activity in chicken rectum, the structure of cCNP was finally determined as follows:

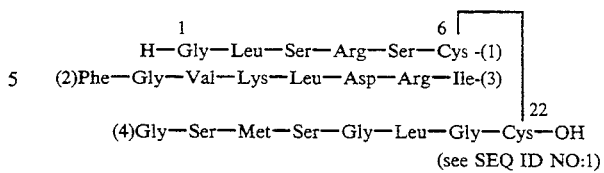

(see SEQ ID NO:1)

wherein (1) and (2), (3) and (4) directly bind, and the cystein residues (Cys) at positions 6 and 22 form an intramolecular disulfide bond.

EXAMPLE 3

Biological characteristics of cCNP

A. Relaxant activity of cCNP in chicken rectum

Relaxant activity in chicken rectum was measured in accordance with the method of Kangawa and Currie (Kangawa, K. and Matsuo, H., *Biochem. Biophys. Res. Commun.*, 118, 131–139, 1984; Currie, M. G., Geller, D. M., Cole, B. R., Boylar, J. G., Yusheng, W., Hormberg, S. W. and Needleman, P. *Science*, 221, 71–73, 1983). The values are averages of six repeats. The results are shown in Table 1. In this assay system, cCNP exhibited an activity which was higher than α-hANP and fANP-21, by about 2 to 5times, respectively. Although cCNP lacked the tail sequence at the C-terminal which had been considered to be important for analog peptides in displaying biological activities such as diuretic action (Watanabe, T. X., Noda, Y., Chino N., Nishiuchi, Y., Kumura, T., Sakakibara, S. and Imai, M. *Eur. J. Pharmacol.*, 147, 49–57, 1988), cCNP had a strong relaxant activity which was comparable to pCNP.

TABLE 1

| diuretic peptide | relative activity |
|---|---|
| α-hANP | 100 |
| cCNP | 321 |
| fANP-21 | 47 |
| fANP-24 | 3.7 |
| pCNP | 472 |
| pBNP-20 | 270 |

Relative activity is defined as the activity of equimolar amount of peptides when the activity of α-hANP is 100.

B. Natriuretic action and vasodepressor activity of cCNP

Diuretic action of cCNP was measured in accordance with the method described in Kangawa et al and Sudoh et al (Kangawa, K. et al., *Biochem. Biophys. Res. Commun.*, 118, 131–139, 1984; Sudoh, T., Kangawa, K., Minamino, N. and Matsuo, H. *Nature*, 322, 78–81, 1988). Male SD rats (weight 300–400 g) were anesthetized by intraperitoneally receiving 50 mg/kg pentobarbitol, and a tracheal cannula (PE-240, Cray Adams) was provided to secure an airway. A cannula for measuring the blood pressure (PE-50) was inserted into one of the femoral arteries, and Ringer solution was injected through a cannula (PE-10) inserted into the femoral venous, at a constant rate of 1.8 ml/hr. Urine was collected into a test tube through a bladder cannula of silastic tube (inside diameter 0.02 inch, outside diameter 0.037 inch, Dow Corning). The collection of urine was carried out for 15 min before the administration of the peptides, at 5 min intervals after the administration till 15 min, and then at appropriate time intervals. The effect of the peptides was measured by comparing the amount of the urine samples and the concentration of the electrolyte in the urine samples, as well as by the change of the blood pressure.

In the above assay, a predetermined amount of cCNP was dissolved in 0.1N acetic acid, and neutralized with one tenth volume of 1.3M Tris solution. Then, the solution was diluted with 50 μl of a sterile physiological water, and administered through the cervical vein. As shown in Table 2, the results indicate that cCNP exhibits natriuretic and vasodepressor actions, and further that these actions increase dose dependently.

The natriuretic and vasodepressor actions of cCNP is shown in Table 2, by comparison with α-hANP.

H. *Biochem. Biophys. Res. Commun.*, 168, 863–870, 1990).

The present inventors succeeded in isolating and characterizing a novel biologically active peptide (cCNP) from chicken brains by a RIA system using an anti-CNP antiserum, found that the peptide had a natriuretic action and a vasodepressor activity, and further clarified that the peptide was a new peptide which belonged to CNP.

By the isolation and characterization of cCNP, chicken and mammal are found to have CNPs in common as well as BNPs. This indicates that both peptides

TABLE 2

| peptide | the amount of administration (μg/kg) | excretion urine (%) | Na+ (%) | K+ (%) | Cl− (%) | decrease of blood pressure (%) |
|---|---|---|---|---|---|---|
| α-hANP | 3.0 | 414 ± 46 | 461 ± 41 | 220 ± 22 | 362 + 34 | 9.0 ± 2.5 |
| cCNP | 30 | 153 ± 32 | 160 ± 9 | 145 ± 12 | 171 ± 2 | 4.4 ± 1.9 |
|  | 90 | 261 ± 19 | 193 ± 6 | 163 ± 02 | 214 ± 5 | 0.3 ± 2.0 |
|  | 200 | 293 ± 50 | 385 ± 50 | 174 ± 18 | 338 ± 107 | 11.5 ± 1.5 |

In Table 2, diuretic and natriuretic responses are shown in terms of the amount of the urine, the percentages in the decreases of the excretion of Na+, K+ and Cl− (Means±S.E.M.), in which urine samples were collected separately over 15 min before and after the intravenous injection of the peptides to anesthetized rats. Three to six rats were used for each peptide. Diuretic and natriuretic actions of cCNP were lower by about 1/100 compared to that of α-hANP. In anesthetized rats, cCNP also exhibited a weak vasodepressor action. In a typical experiment, the blood pressure at the contract phase of heart was decreased by about 5% over a period of 30 min by the action of 30 μg/kg of cCNP. These results are very similar to those of pCNP (Sudoh, T., Minamino, N., Kangawa, K. and Matsuo, BNP and CNP have been playing a key role in regulating the homeostatic balance of the body fluid volume and the blood pressure since the early stages of the evolution.

Since the structure of cCNP has been clarified herein, it is expected that the correlation between the structure and the activity of CNPs may be elucidated by comparing cCNP with porcine brain CNP (pCNP) which was already clarified by the present inventors.

As described above, the present invention will contribute to elucidating the physiological role of cCNP as well as the regulation mechanisms of the homeostatic balance of body fluid volume and the blood pressure in vivo.

What is claimed is:

1. An isolated biologically active peptide having the formula:

$$\begin{array}{c} 1 \qquad\qquad\qquad 6 \\ \text{H—Gly—Leu—Ser—Arg—Ser—Cys -(1)} \\ \text{(2)Phe—Gly—Val—Lys—Leu—Asp—Arg—Ile-(3)} \\ \phantom{xxxxxxxxxxxxxxxxxxxxxxxxxxxxxxxxxxx} 22 \\ \text{(4)Gly—Ser—Met—Ser—Gly—Leu—Gly—Cys—OH} \\ \text{(see SEQ ID NO:1)} \end{array}$$

wherein (1) and (2), (3) and (4) directly bind, and the cystein residues (Cys) at positions 6 and 22 form an intramolecular disulfide bond, and an acid addition salt thereof.

* * * * *

SEQUENCE LISTING ( 1 ) GENERAL INFORMATION:

( i i i ) NUMBER OF SEQUENCES: 7

( 2 ) INFORMATION FOR SEQ ID NO:1:

( i ) SEQUENCE CHARACTERISTICS:
        ( A ) LENGTH: 22 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:1:

```
Gly  Leu  Ser  Arg  Ser  Cys  Phe  Gly  Val  Lys  Leu  Asp  Arg  Ile  Gly
 1             5                        10                           15

Ser  Met  Ser  Gly  Leu  Gly  Cys
                20
```

( 2 ) INFORMATION FOR SEQ ID NO:2:

( i ) SEQUENCE CHARACTERISTICS:
        ( A ) LENGTH: 28 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:2:

Ser Leu Arg Arg Ser Ser Cys Phe Gly Gly Arg Met Asp Arg Ile
1               5                   10                  15

Gly Ala Gln Ser Gly Leu Gly Cys Asn Ser Phe Arg Tyr
            20                  25

( 2 ) INFORMATION FOR SEQ ID NO:3:

( i ) SEQUENCE CHARACTERISTICS:
        ( A ) LENGTH: 28 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:3:

Ser Leu Arg Arg Ser Ser Cys Phe Gly Gly Arg Ile Asp Arg Ile
1               5                   10                  15

Gly Ala Gln Ser Gly Leu Gly Cys Asn Ser Phe Arg Tyr
            20                  25

( 2 ) INFORMATION FOR SEQ ID NO:4:

( i ) SEQUENCE CHARACTERISTICS:
        ( A ) LENGTH: 24 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:4:

Ser Ser Asp Cys Phe Gly Ser Arg Ile Asp Arg Ile Gly Ala Gln
1               5                   10                  15

Ser Gly Met Gly Cys Gly Arg Arg Phe
            20

( 2 ) INFORMATION FOR SEQ ID NO:5:

( i ) SEQUENCE CHARACTERISTICS:
        ( A ) LENGTH: 32 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:5:

Ser Pro Lys Thr Met Arg Asp Ser Gly Cys Phe Gly Arg Arg Leu
1               5                   10                  15

Asp Arg Ile Gly Ser Leu Ser Gly Leu Gly Cys Asn Val Leu Arg
            20                  25                  30

Arg Tyr ( 2 ) INFORMATION FOR SEQ ID NO:6:

( i ) SEQUENCE CHARACTERISTICS:
        ( A ) LENGTH: 29 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:6:

Met Met Arg Asp Ser Gly Cys Phe Gly Arg Arg Ile Asp Arg Ile (2) INFORMATION FOR SEQ ID NO:7:

(i) SEQUENCE CHARACTERISTICS:
    (A) LENGTH: 22 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:7:

Gly Leu Ser Lys Gly Cys Phe Gly Leu Lys Leu Asp Arg Ile Gly
   1           5                   10                      15
  Ser Met Ser Gly Leu Gly Cys
                  20